United States Patent [19]

Perloe

[11] Patent Number: 4,615,979
[45] Date of Patent: Oct. 7, 1986

[54] DIAGNOSTIC URINE CULTURE APPARATUS AND METHOD OF USING SAME

[76] Inventor: Mark Perloe, 1026 Faulkner Dr., Claremore, Okla. 74017

[21] Appl. No.: 473,788

[22] Filed: Mar. 10, 1983

[51] Int. Cl.[4] .................. C12M 1/00; C12M 1/24; C12M 1/20
[52] U.S. Cl. .................. 435/287; 435/296; 435/301; 435/809
[58] Field of Search .......... 435/30, 34, 292, 294, 435/296, 299, 287, 301, 809, 810; 128/761, 763, 760, 771, 768; 436/810; 422/57, 58, 61, 102, 104; 211/74

[56] References Cited

U.S. PATENT DOCUMENTS 3,849,256  11/1974  Linder .................. 435/300
3,888,235  6/1975  May et al. .................. 128/761

OTHER PUBLICATIONS

Martin et al., Am. J. Med. Tech., vol. 40, No. 3, pp. 135-137 (1974).

Primary Examiner—Robert J. Warden
Assistant Examiner—Shawn P. Foley
Attorney, Agent, or Firm—J. David Dainow

[57] ABSTRACT

A diagnostic urine culture apparatus for catheterized urine collection, bacterial detection and bacterial identification, includes a culture tube, a typing medium, a tube cap means, a catheter means where the catheter means extends through an annular opening in the cap means and into the interior of the apparatus, the apparatus thus adapted to the collection and culturing of urine with minimal contamination of the sample.

3 Claims, 5 Drawing Figures

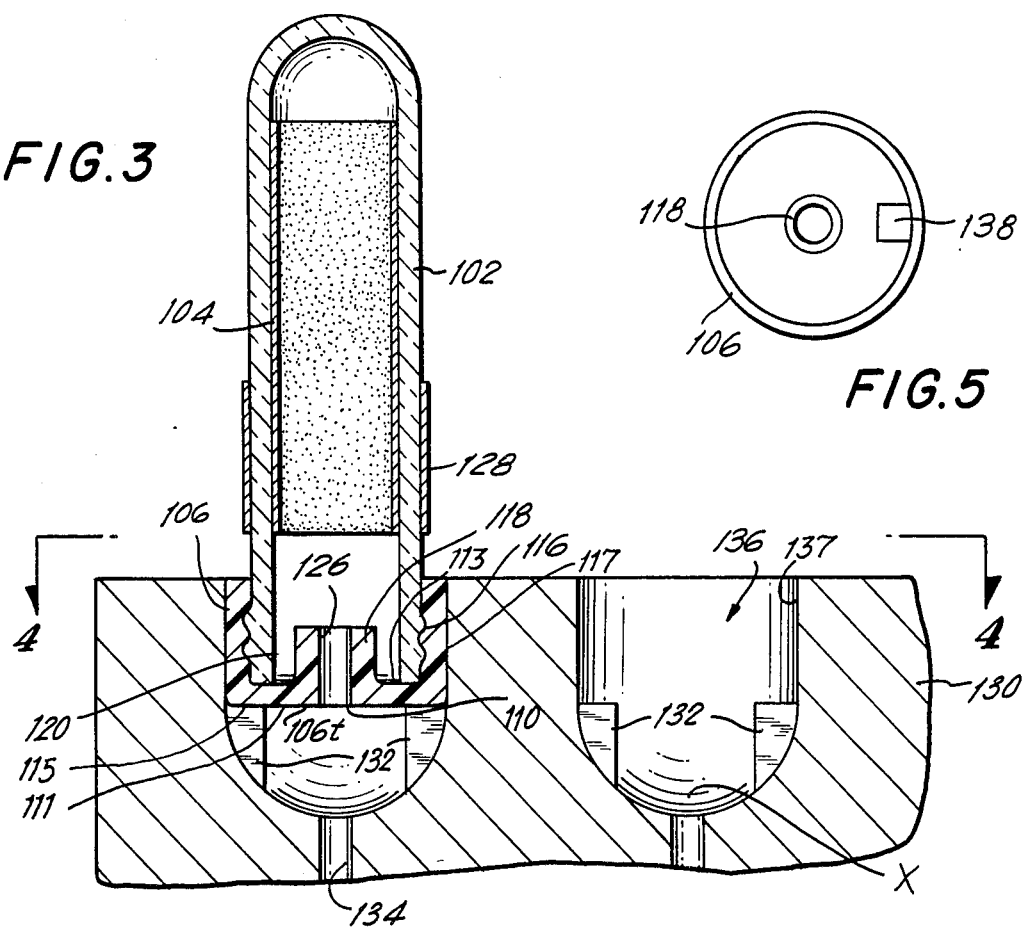
FIG. 3
FIG. 5
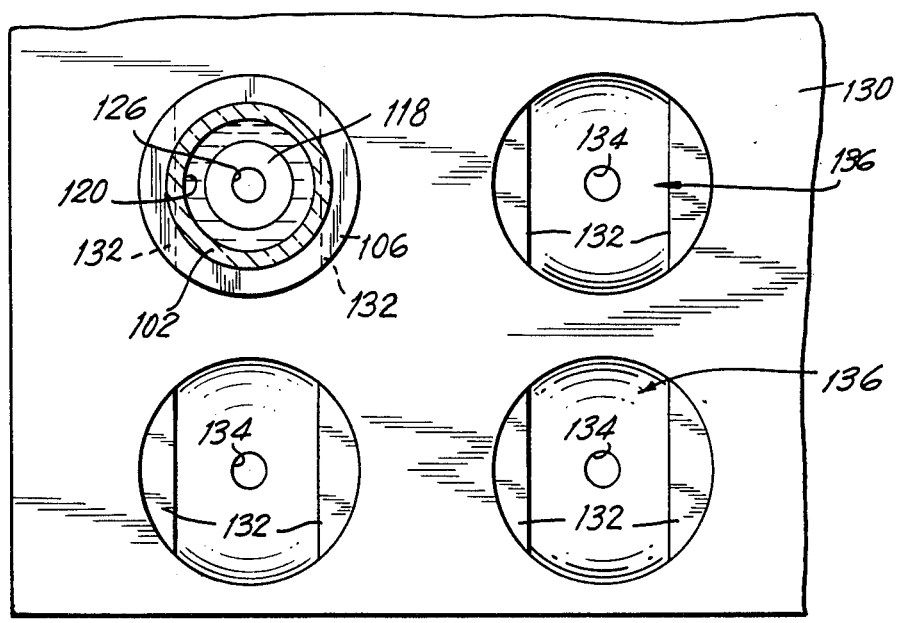
FIG. 4

DIAGNOSTIC URINE CULTURE APPARATUS AND METHOD OF USING SAME

BACKGROUND OF THE INVENTION

The present invention concerns sterile collection and culturing of urine, and more particularly a sterile, disposable device for sterile collection and culture of urine in females.

Infections of the urinary tract are second in incience only to infections in the respiratory tract. Many females have been stigmatized with the misdiagnosis of being susceptible to frequent urinary tract infections as the result of the inaccuracy of present collection and culture methods. It is generally recognized that a high urinary bacterial count is indicative of significant bacterial infection, but when collecting a urine specimen, contaminating organisms or bacteria introduced initially in less than significant numbers can frequently lead to a problem, since urine is a good culture medium. Furthermore, a delay between the time of collection and microbiological examination of only 20 minutes, provides conditions for easy and ready bacterial growth which can result in erroneously high culture colony counts.

Based upon the foregoing, it has been recommended in the past that urine samples be innoculated within an hour after they are collected or be refrigerated immediately. It has also been suggested that a urine collection tube be coated on its inner surface with a culture-indicator medium which would provide a simple and reproducible method for screening of significant bacteria. Thus, this method would eliminate the step of transferring a urine specimen from the original container to a laboratory container, during which transfer additional contamination might occur. This method would yield more reliable results.

In a clinical study, it was found that patients do not receive adequate instruction on catching of a specimen and are often not motivated to provide a good "clean catch" specimen. This is a difficult problem in the female as vaginal discharge is frequently seen coincident with symptoms of urinary tract infection and is almost universally present in pregnant individuals. It is virtually impossible to collect a good clean catch specimen in the presence of significant vaginal discharge. This can result in a false positive culture rate, as high as 80 or 90% false. The following chart shows how this problem was reduced when a known catheter and collector arrangement was used versus an ordinary clean catch device:

| Colonies Detected | Clean Catch % | Catheter Collection % |
|---|---|---|
| >100,000 | 40.1% | 5.8% |
| Method failure | 1 | 2% |

Previous studies found method failures related to design of available culture devices that does not allow for assurance of adequate gas/air exchange to facilitate bacterial growth. This problem has been alleviated in the design of this device. 172 patients were tested and 40.1% of the patients had a positive clean catch culture versus only 5.8% positive in the catheter collection, where >100,000 colonies is considered significant (positive). 22 patients in the clean catch group had multiple organisms and might not have been treated. Therefore, clean catch identified 27.3% of patients requiring therapy (over 100,000 colonies) versus 5.8% of catheterized tests showing the same need of therapy. If 100,000 colonies is considered the threshhold, more than four times the number of patients actually requiring therapy would have been given thereapy based on the clean catch results compared to the catheterized test results.

Even with the above stated improvements, however, there is still considerable opportunity for contamination of samples occasioned by the female anatomy and elevated bacterial colony counts due to delay in culturing the urine. It is therefore an object of the present invention to minimize these sources of error.

It is another object of the present invention to reduce contamination by reducing the number of containers used in taking specimens.

Catheterization has been thought to cause urinary tract infection, especially in pregnant patients. However, a study using a known catheter collecting system did not result in an increase in symptomatic urinary tract infections in pregnant individuals.

Furthermore, it is well known that asymptomatic bacteria in pregnancy may be associated with premature labor and a 50% risk of pyelonephritis. Many authors have recommended screening for bacteria in pregnant patients. Problems with present methods include cost, contamination, risk of inducing infection, personal time and perhaps most important, delay in initiating therapy. In one study, (Harris OBGYN,Vol. 53, pages 71-73) 28% of the cases of pyelonephritis occurred in a population of pregnant women screened for bacteria. These cases were theoretically preventable and were attributed to method failure. Greater than half of failures were related to a delay between collecting the urine specimen and being made aware of the culture results. My new system should prevent those failures, and results can be obtained in 24 hours. Thus, although testing is advised, the risk of taking contaminated samples reduces the value of the test results and often requires re-testing. A study looking at the cost effectiveness of this method of screening for urinary tract infection in pregnancy found a 61% cost savings over no screening method and greater than 52% saving over standard methods.

SUMMARY OF THE INVENTION

The present invention overcomes these and other difficulties by providing a new diagnostic urine culture apparatus for catheterized urine collection, bacterial detection and bacterial identification all in one basic device. The result is that contamination is further minimized, lab time is reduced, expense is reduced, and accuracy is greatly improved.

The present apparatus is ideally suited for standard urine collection, including screening urine of female patients presenting symptoms of upper urinary tract infection and for monitoring patients subject to recurrent infections. It eliminates the need for accessory collection vessels thereby removing a possible source of contamination. More importantly, false counts due to reproduction of bacteria in standing urine are avoided. Immediately after the specimen is produced into the apparatus and the tube has been emptied, culturing of discrete colonies proportional to the actual initial bacterial population will begin. This device may also provide an accurate bacterial count with class identification of the infecting organism by color differentiation. The latter is of particular importance in that discrete colonies can be removed for staining and subculturing for further identification or sensitivity testing.

One of the greatest advantages of the present invention is that it facilitates uncontaminated catching of urine in a culturing tube which is designed to facilitate rendering of test results in approximately 24 hours in an incubator or 60 hours at room temperature. This can be done with the present invention with great accuracy and is fully processable in a doctor's office.

Further and still other objects and advantages of this invention will become more clearly apparent by reference to the following description when taken in conjunction with the accompanying drawings in which:

FIG. 3 is a cross-sectional side view of a tray for and in use with, the present invention;

FIG. 4 is a partial top view of the tray of FIG. 3; and

FIG. 5 is a bottom plan view of the interior side of an alternative embodiment of the cap of the present invention.

DETAILED DESCRIPTION

Figures 1, 2:
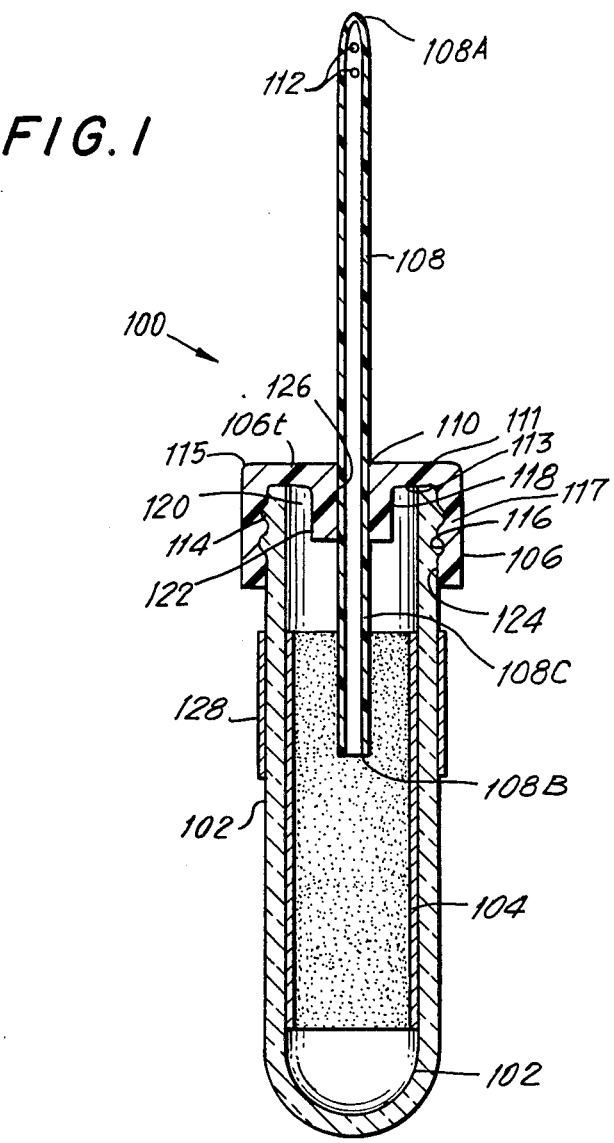
FIG. 1 is a cross-sectional view of the present invention.
FIG. 2 is a front view of a label used in conjunction with the present invention.

Referring now to the figures and particularly to FIG. 1, numeral 100 identifies the present invention, wherein the collection and culture tube 102 is seen with a typing medium (for incubation, detection and identification of bacterial colonies) indicated as 104 within tube 102. Cap 106 is seen in FIG. 1 attached to the open end of tube 102, and catheter 108 is seen inserted in opening 110 of cap 106. End 108A of catheter 108 is closed; however, openings (perforations) 112 are provided near 108A end. Catheter 108 is open-ended at its other end 108B; the open end portion 108C is shown extending within tube 102. The cap includes an annular wall 117, and a top wall 111 which has an inner surface 113 and a generally planar outer surface 115. Cap opening 110 is designed to allow predetermined gas/air exchange to facilitate growth of colonies.

Cap 106 will engage tube 102 in any secure method, such as by screw-on or snap-on design. As shown in FIG. 1, tube 102 is provided with tapered threads 114 which meet with tapered threads 116 of cap 106. Cap 106 is provided with protuberance 118 extending from the inner surface 113 of the cap; this protuberance is formed as a raised cone-like section creating reservoir area 120 defined by the cooperation of exterior wall 122 (of protuberance 118) and interior wall 124 (of cap 106). The protuberance is substantially perpendicular to the cap surface 106t. Reservoir 120 is disposed to receive the open end of tube 102 without critical loss of reservoir volume.

Catheter 108 is designed and selected in configuration so as to firmly and snugly fit into the channel created at opening 110 within protuberance 118. The channel is designated as element 126, as seen in FIG. 3.

FIG. 1 shows the cooperation of catheter 108 with cap 106 as the catheter has been inserted in and extends through opening 110 of protuberance 118 and is carried by channel 126. FIG. 5 shows a front view of an alternative cap 106 showing protuberance 118, which is an end view of channel 126. Also shown is projection 138, which, in this alternative embodiment, would permit closure of the device to a predetermined condition, according to gas/air exchange desired at the cap/tube junction.

As seen in FIG. 3 medium 104 is affixed to a substantial portion of the interior wall tube 102, in any known method. Conventional media are employed which facilitate culturing of bacterial colonies, as well as allowing detection and counting of colonies. Such media may also be provided with known color coded indicators to permit class indenfication of any infecting organisms.

In operation, catheter 108 is extending through opening 110 at channel 126. This combination (as seen in FIG. 1) is then attached to tube 102 at its open end. The tube has been coated with typing medium 104 on its interior wall. By attaching cap 106 to tube 102 with the open end portion of the catheter 108C being inserted within the tube, a sterile environment is now created within the tube (assuming attachment has been done in sterile conditions). Unit 100 is then packaged in sterile packaging (not shown).

In use, unit 100 is removed from its sterile package and the female patient is prepared for insertion of the catheter. Specifically, labia are spread followed by swabbing of the urethal meatus with an antiseptic swab. This is followed by insertion of the free but perforated end 108A of the catheter into the urinary tract until urine flow is noted in the closed tube. (Specifically, urine flows from the bladder, through openings 112, through catheter 108, then out end 108B and into tube 102.) Thereafter withdrawal of the catheter from the urinary tract and from the apparatus is accomplished, the catheter being discarded. Next, cap 106 is removed from the tube and the urine is poured out, while the user avoids contaminating the inside surfaces of the tube. The cap is then restored to the tube to a desired tightness. Control of this tightness will control gas exchange and drying time.

Next, the tube with cap on is preferably placed in cap-down position in an incubation area. Incubation of the specimen follows, with counting of the resultant colonies following thereafter. (It is noted that it is preferable that before removing cap and discarding urine, the urine should be swirled in the tube to assure full coating of the typing medium.)

When the apparatus is placed in cap-down position any remaining urine will be able to collect in reservior 120. This will not block the channel opening 110, which permits gas exchange during incubation. Finally, reading of the colonies appearing on the medium can be done with ease, and results can be recorded on a label, as shown in FIG. 2. It is contemplated that this label will be provided with facility for easy removal from the tube and for direct attachment thereof to a patient's chart.

While the present invention has been described in particular preferred embodiments, it should be understood that other embodiments can be made within the spirit and scope of this invention and that the foregoing description is to be understood as merely illustrative.

What is claimed is:

1. In combination, a diagionistic culture apparatus for catheterized urine collection, bacterial detection and identification, and an incubation tray for use with the culture apparatus, said culture apparatus comprising:
   a culture tube having interior and exterior surfaces, a closed bottom end, and open top end;
   typing medium coated on the interior surface of said tube for detecting and identifying bacteria;
   a cap at least in part closing the open end of the culture tube, said cap including a top wall having a generally planar outer surface, an annular wall depending from the top wall, and a channel extending through the top wall; and catheter means for collecting a urine specimen, said catheter means extending through the cap channel such that urine may pass through said catheter means into said culture tube for diagnostic analysis;

an incubation tray comprising:

at least one hollow cavity recessed in a surface of said tray, said at least one hollow cavity including support means for supporting said culture tube, and ventilation means in said tray, said ventialtion means communicating with said cap channel for gas exchange between the ambient atmosphere and the culture medium.

2. A combination of culture tube and incubation tray as claimed in claim 1, wherein said at least one hollow cavity includes a shoulder extending from a surface of said cavity, said culture tube when received in said at least one hollow cavity having said planar top surface of said cap resting on said shoulder, the periphery of said cavity along said one tray surface, the periphery of cavity along said one tray surface corresponding with the outer periphery of said capped culture tube, said culture tube being partially inserted in said cavity when resting on said shoulder.

3. The combination as claimed in claim 1, wherein said ventillation means includes an outlet channel between said at least one hollow cavity and the lower surface of said tray, said channel through said culture tube cap being displaced at least in part from said shoulder, allowing air exchange between said culture tube, said cavity and said ambient atmosphere.

* * * * *

UNITED STATES PATENT AND TRADEMARK OFFICE
CERTIFICATE OF CORRECTION

PATENT NO.  :  4,615,979

DATED       :  October 7, 1986

INVENTOR(S) :  Mark Perloe

It is certified that error appears in the above-identified patent and that said Letters Patent is hereby corrected as shown below:

It is respectfully requested that the above patent be corrected as follows:

Column 2, line 3, change "threshhold" to --threshold--.

Column 4, line 41, after "medium" insert the following paragraphs:

Figs. 3 and 4 show a preferred tray 130 for use with the culture tube, wherein cap top surface 106 t is placed into a space 136 upon support means defined as opposing a planar shoulders 132. The space 136 is defined as a hollow cavity recessed in a surface of said tray, said cavity including said support means for supporting said culture tube. The annular tray wall 137 receives and surrounds the annular cap wall 117 in supporting

UNITED STATES PATENT AND TRADEMARK OFFICE
CERTIFICATE OF CORRECTION

PATENT NO. : 4,615,979
DATED : October 7, 1986
INVENTOR(S) : Mark Perloe

It is certified that error appears in the above-identified patent and that said Letters Patent is hereby corrected as shown below:

relationship, and the planar shoulders 132 receive the planar cap surface 111, thereby allowing the top surface of the cap to rest on said shoulders. The periphery of the hollow cavity along the tray surface corresponds with the outer periphery of said capped culture tube, said culture tube being partially inserted in said cavity when resting on said shoulders.

The space 136 includes an area "X" defined by an annular wall 137 and the opposing shoulders 132. Area "X" communicates with outlet channel 134 and cap opening 110 to effect gas exchange between the atomsphere and the culture medium. Other arrangements are possible for permitting gas exchange. For example, ventillation menas can be provided by an outlet channel (134) between the hollow cavity and the lower surface of the

UNITED STATES PATENT AND TRADEMARK OFFICE
CERTIFICATE OF CORRECTION

PATENT NO. : 4,615,979
DATED : October 7, 1986
INVENTOR(S) : Mark Perloe

Page 3 of 3

It is certified that error appears in the above-identified patent and that said Letters Patent is hereby corrected as shown below:

incubation tray, the cap channel through the culuture tube cap being displaced at least in part from said shoulder, allowing air exchange between said culture tube, said hollow cavity and the atmosphere.

Signed and Sealed this

Twentieth Day of January, 1987

Attest:

DONALD J. QUIGG

*Attesting Officer*     *Commissioner of Patents and Trademarks*